(12) United States Patent  
Landsberger et al.

(10) Patent No.: US 10,874,848 B2  
(45) Date of Patent: Dec. 29, 2020

(54) METHOD AND DEVICE FOR PROVIDING STIMULATION TO A COCHLEA

(71) Applicant: New York University, New York, NY (US)

(72) Inventors: David M. Landsberger, New York, NY (US); J. Thomas Roland, New York, NY (US)

(73) Assignee: NEW YORK UNIVERSITY, New York, NY (US)

( * ) Notice: Subject to any disclaimer, the term of this patent is extended or adjusted under 35 U.S.C. 154(b) by 187 days.

(21) Appl. No.: 16/015,041

(22) Filed: Jun. 21, 2018

(65) Prior Publication Data

US 2018/0369571 A1    Dec. 27, 2018

Related U.S. Application Data

(60) Provisional application No. 62/523,478, filed on Jun. 22, 2017.

(51) Int. Cl.
*A61N 1/05* (2006.01)
*A61N 1/36* (2006.01)

(52) U.S. Cl.
CPC ....... *A61N 1/0541* (2013.01); *A61N 1/36039* (2017.08)

(58) Field of Classification Search
CPC .......................... A61N 1/0541; A61N 1/36039
See application file for complete search history.

(56) References Cited

U.S. PATENT DOCUMENTS

2016/0015975 A1\* 1/2016 Dueck ................ A61N 1/36036
607/57

OTHER PUBLICATIONS

Baumann et al., "Pulse Rate Discrimination with Deeply Inserted Electrode Arrays", Hearing Research, vol. 196, 2004, pp. 49-57.
Baumann et al., "The Cochlear Implant Electrode-Pitch Function", Hearing Research, vol. 213, 2006, pp. 34-42.
Stakhovskaya et al., "Frequency Map for the Human Cochlear Spiral Ganglion: Implications for Cochlear Implants", Journal of the Association for Research in Otolaryngology, vol. 8, 2007, pp. 220-233.

(Continued)

*Primary Examiner* — Paula J Stice
(74) *Attorney, Agent, or Firm* — Fay Kaplun & Marcin, LLP (57) ABSTRACT

A cochlear implant includes an electrode array having a plurality of electrode contacts arranged along at least a portion of a length of an electrode array, and a processing arrangement configured to map at least one electrode contact to first and/or second mappings. The first mapping provides a first electrical stimulation from the electrode contact to a first ground electrode positioned external to a patient's cochlea to stimulate hearing at a first location in the cochlea positioned adjacent to the electrode contact when the implant is inserted into the cochlea. The second mapping provides a second electrical stimulation from the electrode contact to the second ground electrode to stimulate hearing at a location in the cochlea positioned further towards the apex of the cochlea as compared to a distal end of the electrode array when the implant is inserted into the cochlea.

13 Claims, 5 Drawing Sheets

(56) References Cited

OTHER PUBLICATIONS

Middlebrooks et al., "Selective Electrical Stimulation of the Auditory Nerve Activates a Pathway Specialized for High Temporal Acuity", The Journal of Neuroscience, vol. 30, No. 5, 2010, pp. 1937-1946.
Kileny et al., "Performance With the 20 + 2L Lateral Wall Cochlear Implant", The American Journal of Otology, vol. 19, No. 3, 1998, pp. 313-319.
Buchman et al., "Influence of Cochlear Implant Insertion Depth on Performance: A Prospective Randomized Trial", Otology & Neurotology, vol. 35, 2014, pp. 1773-1779.
Landsberger et al., "The Relationship between Insertion Angles, Default Frequency Allocations, and Spiral Ganglion Place Pitch in Cochlear Implants", Ear Hear, vol. 36, 2015, 15 Sheets.
Landsberger et al., "Qualities of Single Electrode Stimulation as a Function of Rate and Place of Stimulation with a Cochlear Implant", Ear Hear, vol. 37, 2016, 23 Sheets.

\* cited by examiner

METHOD AND DEVICE FOR PROVIDING STIMULATION TO A COCHLEA

PRIORITY CLAIM

The present application claims priority to U.S. Provisional Application Ser. No. 62/523,478 entitled "Method and Device for Providing Stimulation to a Cochlea" filed on Jun. 22, 2017, the entire contents of which is hereby incorporated by reference herein.

BACKGROUND

In the normal hearing human ear, the cochlea is the anatomical structure in which physical vibrations are transformed into electrical impulses along the auditory nerve. The cochlea is a snail-shaped structure that typically wraps about 2.75 turns from the bottom (base) to the top (apex). The cochlea is arranged tonotopically in that frequencies are encoded such that the lowest frequencies are encoded near the apex and the highest frequencies are encoded at the base.

Cochlear implants provide hearing to profoundly deafened individuals by converting sound information into an electrical code that the brain can understand. This happens after an array of electrode contacts are correctly placed into the cochlea. Each of the electrode contacts on the array stimulates a different part of the cochlea and therefore, due to the tonotopic organization of the cochlea, provides a different pitch. Typically, the electrode arrays are inserted from the cochlear base (either by the round window or a cochleostomy) and then wrap up the cochlea. Most electrode arrays are only inserted about 1 to 1.25 turns into the cochlea which allow stimulation of the cochlear regions that typically represent approximately 700 Hz and higher. Longer electrode arrays (such as the MED-EL Flex28) can reach deeper into the cochlea and stimulate regions representing lower frequencies. However, the longer the electrode array, the more chance there is to damage the structures of the cochlea during insertion and the more difficult the array is to insert.

Therefore, there is a need for cochlear implants to provide improved electrical stimulation of the cochlea such that audio signals having sounds at lower frequencies can be mapped to an electrode array of a cochlear implant to improve quality of hearing stimulated by the cochlear implant.

SUMMARY OF THE INVENTION

One exemplary embodiment of the present invention relates to a cochlear implant. The cochlear implant may comprise a first ground electrode configured to be positioned external to a cochlea of a patient, and a second ground electrode configured to be positioned in or adjacent to an apex of a cochlea of a patient. The first ground electrode may be a plate electrode. The second ground electrode may be a ball electrode. The cochlear implant may also comprise a flexible electrode array having a distal end and a proximal end defining a length therebetween. The electrode array may be biased to a snail-like coiled shape. In one embodiment, the length of the electrode array may be configured to be inserted by no more than about 450 degrees into the cochlea towards the apex, or by no more than about 360 degrees into the cochlea towards the apex. The electrode array may comprise a plurality of electrode contacts arranged along at least a portion of the length of the electrode array. The electrode array may be configured to be inserted into the cochlea such that the distal end of the electrode array advances from a base of the cochlea towards the apex of the cochlea. The cochlear implant may further comprise a processing arrangement configured to map at least one electrode contact to a first mapping for providing a first electrical stimulation from the electrode contact to the first ground electrode to stimulate hearing of the patient at a first location in the cochlea, and a second mapping for providing a second electrical stimulation from the electrode contact to the second ground electrode to stimulate hearing of the patient at a second location in the cochlea. The first electrical stimulation and/or the second electrical stimulation may be a monopolar electrical stimulation. The first location in the cochlea is positioned adjacent to the electrode contact when the implant is inserted into the cochlea in an operating position, and the second location in the cochlea is positioned further towards the apex of the cochlea as compared to the distal end of the electrode array when the implant is in the operating position.

In one aspect of the invention, a method for electrically stimulating a cochlea of a hearing-impaired patient and a non-transitory computer-readable storage medium including a set of instructions executable by a processor, the set of instructions, when executed by the processor, causing the processor to perform operations for electrically stimulating a cochlea of a hearing-impaired patient are provided. The method comprises a first step for decomposing an audio input signal into a plurality of frequency channels. A first one of the frequency channels correspond to a first range of frequencies and a second one of the frequency channels correspond to a second range of frequencies. The second range of frequencies may be lower than the first range of frequencies. Next, the method comprises a step controlling generation of a first electrical stimulation from an electrode contact inserted into the cochlea of the patient to a first ground electrode positioned external to the cochlea to stimulate hearing of the patient within the first frequency channel, and of a second electrical stimulation from the electrode contact to the second ground electrode to stimulate the hearing of the patient within the second frequency channel. The first frequency channel is stimulated at a first portion in the cochlea. The first portion is positioned adjacent to the first electrode contact. The second frequency channel is stimulated at a second portion in the cochlea. The second portion is located further towards the apex of the cochlea as compared to the electrode contact.

In another aspect of the invention, a method for electrically stimulating a cochlea of a hearing-impaired patient is provided. The method comprises first inserting an electrode array having a distal end and a proximal end defining a length therebetween into the cochlea of the patient such that the distal end of the electrode array is advanced from a base of the cochlea towards the apex of the cochlea. In some embodiments, the electrode array may be inserted by cochleostomy into the cochlea by no more than about 450 degrees towards the apex, or by no more than about 360 degrees toward the apex. The electrode array may comprise a plurality of electrode contacts arranged along at least a portion of the length of the electrode array. The method also comprises positioning a first ground electrode external to the cochlea and a second ground electrode in or adjacent to an apex of a cochlea of a patient. The method then comprises decomposing an audio signal into a plurality of frequency channels. A first one of the frequency channels correspond to a first range of frequencies and a second one of the frequency channels correspond to a second range of frequencies. The second range of frequencies may be lower than the first range of frequencies. The method further comprises generating a first electrical stimulation from a first one of the electrode contacts to the first ground electrode to stimulate hearing of the patient within the first frequency channel and a second electrical stimulation from the first one or a second one of the electrode contacts to the second ground electrode to stimulate the hearing of the patient within the second frequency channel. The first frequency channel is stimulated at a first portion in the cochlea. The first portion is positioned adjacent to the electrode contact. The second frequency channel is stimulated at a second portion in the cochlea. The second portion is located further towards the apex of the cochlea as compared to the distal end of the electrode array.

In a further aspect of the invention, a method for fitting a cochlear implant and a non-transitory computer-readable storage medium including a set of instructions executable by a processor, the set of instructions, when executed by the processor, causing the processor to perform operations for fitting a cochlear implant are provided. The method comprises administering a first audio signal having a first frequency to a patient implanted with the cochlear implant. The implant comprising a first ground electrode positioned external to a cochlea of a patient, a second ground electrode positioned in or adjacent to an apex of a cochlea of a patient, and an electrode array having a distal end and a proximal end defining a length therebetween, the electrode inserted into the cochlea such that the distal end of the electrode array is advanced from a base of the cochlea towards the apex of the cochlea. The method also comprises mapping a first one of the electrode contacts with the first ground electrode for imparting a first electrical stimulus configured to stimulate hearing of the patient at a first frequency channel. The method then comprises administering a second audio signal having a second frequency to a patient implanted with the cochlear implant. The method further comprises mapping the first electrode contact with the second ground electrode for imparting a second electrical stimulus configured to stimulate hearing of the patient at a second frequency channel having a lower frequency range as compared to the first frequency channel. The second frequency channel may be stimulated by the first electrode contact to an apical location in the cochlea positioned further towards the apex of the cochlea as compared to the distal end of the electrode array.

These and other aspects of the invention will become apparent to those skilled in the art after a reading of the following detailed description of the invention, including the figures and appended claims.

DETAILED DESCRIPTION

Cochlear implants may restore the ability to hear to deaf or partially deaf individuals by providing electrical stimulation to the auditory nerve corresponding to the audio signal. For example, a cochlear implant may comprise an array of electrodes that are configured for insertion into the cochlea. The electrode array from a cochlear implant may comprise multiple contacts along the array. In addition, the cochlear implant may comprise a ground electrode. Each of the contacts on the array may be paired with a ground electrode and configured to stimulate a different part of the cochlea. Because the cochlea is arranged such that each location represents a different frequency (i.e., tonotopic organization of the cochlea), each pair of electrode contact and ground electrode may be perceived as having a different "place pitch" and therefore, may be used to represent a different frequency region in clinical fittings.

The most common cochlear implant array designs are built to be inserted only about 360 to 450 degrees into the cochlea. In the normal hearing ear, the region that is represented by one of these electrode arrays typically encodes frequencies of about 800 Hz and above. However, as cochlear implants typically encode a range of about 200-8000 Hz, a mismatch may be created between the frequency that would be expected at a specific location by a normal hearing cochlea and the frequency that is delivered to a cochlear implant at that location.

Figure 1:
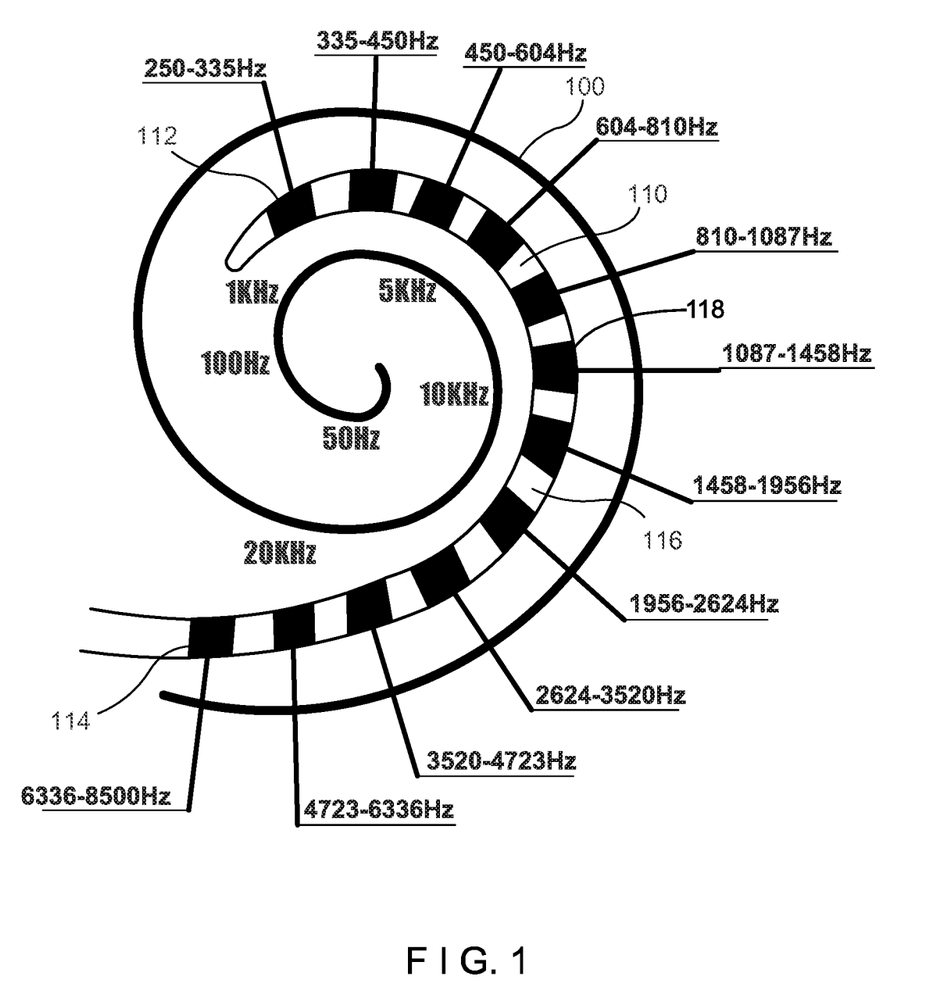
FIG. 1 shows a schematic of a cochlea where a cochlear implant having an array of electrode contacts is inserted therein.

As shown in FIG. 1, a schematic of a cochlea 100 where a cochlear implant 110 having an array 116 of electrode contacts 118 is inserted therein. The cochlear implant 110 may further comprise a microphone for receiving input signals, e.g., sounds to be stimulated to the patient, a signal processor for receiving and processing the input signals, and one or more computer processors for analyzing the input data and/or controlling the electrical stimulation that is imparted to the patient via the electrode contacts. In some embodiments, the array 116 of electrode contacts 118 may be operably connected an external component (e.g., implant package) of the cochlear implant 110 that, when in use, is positioned external of the cochlea 100, in particular, external of the ear of the patient, such as, for example, reversibly attached to behind an ear of the patient. The external component may comprise the microphone, the signal processor, and/or one or more computer processors. The microphone may comprise any suitable sensor for detecting and receiving an analog audio signal from an external environment. The microphone may be operably connected to a signal processor so as to transmit the analog audio signal to the signal processor. The signal processor may comprise any suitable component for converting the analog audio signal to a digital signal. The signal processor may also further process the signal to de-noise, amplify certain desired portions, or otherwise modify the incoming signal. The digital signal or modified digital signal may then be transmitted as input data to one or more computer processors. The one or more computer processors may be configured to analyze this input data and/or control electrical stimulation of the cochlea 100 delivered by the cochlear implant 110, more particularly, via the array 116 of electrode contacts 118. In particular, the one or more computer processors may analyze the input data and generate instructions for stimulating electrical signals via the array 116 of electrode contracts 118 corresponding to the input date such that the patient is stimulated to hear a sound corresponding to the analog audio signal detected by the microphone. The processors may also be configured to perform a portion or the entirety of the methods described in the present application.

As shown in FIG. 1, the frequency values identified in the drawing on the interior portion of the snail-like structure of the cochlea 100 correspond to frequencies that are expected at a given location in the normal ear (i.e., either the characteristic frequencies along the Organ of Corti or Spiral Ganglion). The frequency ranges shown on the exterior portion of the snail like structure of the cochlea in the drawing correspond to an exemplary embodiment of frequencies that may be provided by electrical stimulation of each of the electrode contacts 118 in the array 116, as shown in FIG. 1. The more apically inserted electrode contacts 118 correspond to lower frequency ranges, whereas more basally located electrode contacts 118 correspond to higher frequency ranges. As shown in the example of FIG. 1, the most apical electrode contact 112 imparts an electrical signal that stimulates hearing in the patient corresponding to an input signal in the range of 250-335 Hz. In other embodiments, the most apical electrode contact 112 may impart an electrical signal that stimulates hearing in the patient corresponding to an input signal in the range of 250-500 Hz. In contrast, the most basal electrode contact 114 shown in the example of FIG. 5 may impart an electrical signal that stimulates hearing in the patient corresponding to an input signal in the range of 6336-8500 Hz. In another embodiment, the most basal electrode contact 114 may impart an electrical signal that stimulates hearing in the patient corresponding to an input signal in the range of 3800-6800 Hz. As can be seen in FIG. 1, there may be a mismatch between frequencies expected at any given cochlear location in a normal ear as compared to the frequencies stimulated by the electrical signals imparted by each of the cochlear implant electrode contacts 118. Therefore, if the electrode array 116 is moved more or less apically within the cochlea 100, or if the length of the electrode array 116 is changed, the relationship between place of stimulation and the frequency provided at that location can be modified/further distorted. Furthermore, after the surgery, the locations of the electrode contacts 118 and places of stimulation corresponding to each electrode contact 118 are surgically fixed, but the frequency values of the filters used in the cochlear implant 110 may be further modified and may be arbitrarily re-mapped as desired.

Selecting an appropriate length of an electrode array is a tradeoff. The longer the electrode array, the more chance there is for damage of the cochlea which can lead to either loss of any remaining residual hearing or damage to the structure of the cochlea, which is necessary for good functioning of a cochlear implant. However, it is believed that longer electrode arrays provide better performance than shorter electrode arrays. For example, a cochlear implant having a shorter electrode array may provide poorer speech in noise scores than a different cochlear implant having longer electrode arrays when only electrical stimulation is used. As another example, electrode arrays that are designed to be inserted beyond 450 degrees may provide better performance than similar arrays inserted less than approximately 450 degrees.

Furthermore, it is believed that stimulation deep into the second cochlear turn is beneficial. In particular, apical stimulation (e.g., beyond 450 degrees) is believed to provide better temporal discrimination than stimulation at a location in the first cochlear turn. It is also believed that the sound quality of low rates of stimulation (i.e., rates useful for temporal quality) provide a poor sound quality in the first cochlear turn, but has a much better sound quality in the apex. Consistently, it is further contemplated that apical stimulation activates a pathway specialized for temporal coding.

In a cochlear implant, stimulation may be in a "monopolar mode" in which current flows from an intra-cochlear electrode to a ground electrode, such as, for example, an extra-cochlear ground electrode. However, monopolar and other modes of stimulations are both contemplated by the present invention. Although only one ground electrode is needed for monopolar stimulation, exemplary cochlear implants of the present application may have two ground electrodes so that one can be used as a ground electrode for stimulation while another ground electrode can be used for recording. One ground electrode may be positioned external to the cochlea, such as, for example, on an implant package. Another ground electrodes may be positioned at various places in the cochlear implant system, such as, for example, internal to the cochlea when the device is in use. In one embodiment, the cochlear implant may comprise at least two ground electrodes that are configured to be placed at different parts of an ear into which the cochlear implant is inserted in an operating configuration. For example, one ground electrode may be positioned outside of a cochlea and another ground electrode may be positioned on, within, or near an apex of the cochlea. Furthermore, each of the electrode contacts on the array may be configured to be paired with one or more ground electrodes to provide stimulation at a predetermined frequency or frequency range to the cochlea. In some embodiments, the second ground electrode may be connected to or attached to a wire separate from the electrode array that is inserted into the cochlea. This second ground electrode may be placed under the temporalis muscle. Although most electrodes only stimulate regions representing about 700 Hz and above, lower frequencies may be presented by an exemplary cochlear implant of the present invention but at a cochlear location different from which the normal auditory system would expect to hear that frequency. For example, a 240 Hz stimuli may be provided to a contact positioned in an operating configuration at a cochlear location expecting approximately 725 Hz (which is about 3 octaves higher). Similarly, a 1000 Hz stimuli could be presented to a cochlear location expecting approximately 1670 Hz. It is believed that if deeper stimulation could be achieved then sound quality would improve, and subjects would perform better (and quicker reach asymptotic performance) on speech in noise tasks.

The present application describes a new surgical approach in which a ground electrode affixed on its own lead may be placed near or on the apex of the cochlea via an apical cochleostomy. Once the ground electrode is placed in the apex, stimulation of an electrode along an electrode array placed within the cochlea can be paired with either a ground electrode on an implant package (e.g., at an extra-cochlear position) or a ground electrode located at or near the cochlear apex. When current flows from the electrode array to the apical ground electrode, it is expected to stimulate neurons located more apically than neurons stimulated by current flowing from the electrode array to an extracochlear ground electrode located on the package (which is the typical path). As a result, when stimulating using an apical ground electrode, parts of the cochlea used to encode lower frequencies should respond by producing a lower pitch than when stimulating with the extra-cochlear ground electrode. This may be used to improve speech in noise performance and sound quality without requiring a new hardware design or a longer electrode array which risks additional damage to cochlear structure damage.

Figure 2:
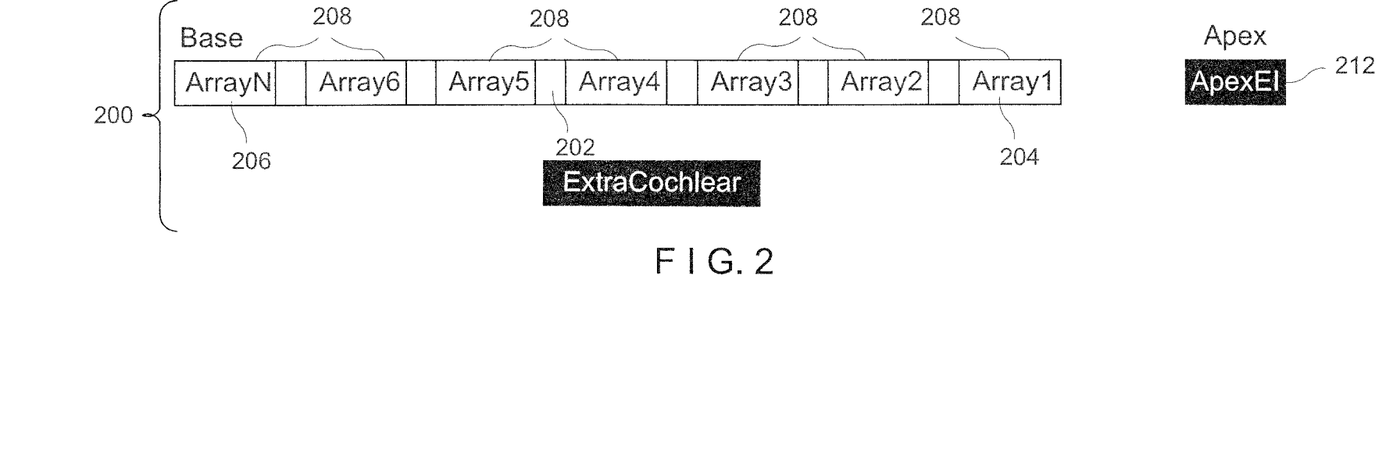
FIG. 2 shows an exemplary embodiment of a cochlear implant comprising an electrode and two ground electrodes.
Figure 3:
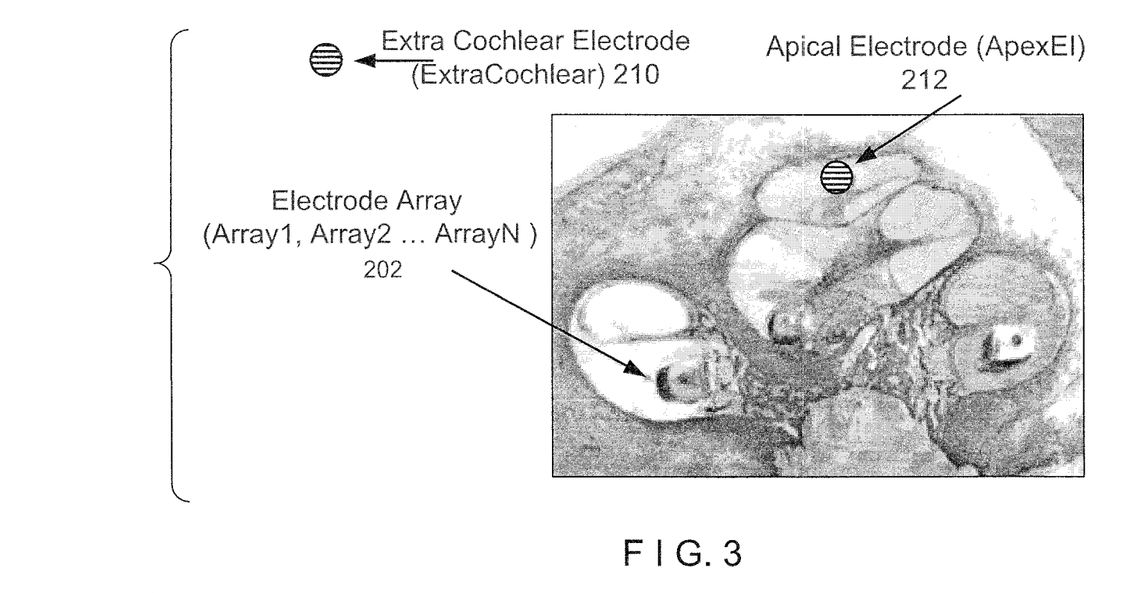
FIG. 3 shows an exemplary embodiment of a placement of an apical ground electrode relative to an electrode array and an extra cochlear electrode.

In one exemplary embodiment, a cochlear implant 200 for providing apical stimulation may be provided, such as, for example, that shown in FIG. 2. FIG. 3 shows an exemplary embodiment of a placement of an apical ground electrode 212 relative to an electrode array 202 and an extra cochlear electrode 210 within a cochlea of a patient. The cochlear implant 200 may include an electrode array 202 formed from a flexible material (e.g., an elastic material) that that is biased to a coiled shape corresponding to the snail-like shape of the cochlea. For example, the electrode array 202 may comprise a flexible non-conductive substrate on which a plurality of electrode contacts 208 may be attached, such as, a shape-memory material, e.g., thermoplastic elastomers, silicone, etc. The electrode array 202 may be sufficiently flexible such that the electrode array 202 may be extendable to an elongated shape, as shown in FIG. 2, to facilitate insertion of the electrode array 202 into the cochlea. The electrode array 202 may have a distal end 204 and a proximal end 206 defining a length therebetween. In an operating configuration, the distal end 204 of the electrode array 202 may be inserted in a direction towards the apex of the cochlea. The electrode array 202 may have any suitable length for insertion into the cochlea. In particular, the electrode array 202 may have a length configured for insertion into the cochlea by one turn, one and a quarter turns, or one and a half turns from a base the cochlea and into the cochlea, in a direction towards the apex of the cochlea. When the electrode array is inserted into the cochlea, a distal end 204 of the electrode array is advanced from the base through the turn(s) towards the apex. In one exemplary embodiment, the electrode array 202 may have a length configured for insertion into the cochlea by no more than about 540 degrees, 450 degrees, or 360 degrees into the cochlea towards the apex. For example, the electrode array 202 may have an extended length (i.e., when the electrode array 202 is uncoiled and extended lengthwise) less than approximately 31 mm, less than approximately 28 mm, less than approximately 25 mm, less than approximately 20 mm, or less than approximately 16 mm.

The electrode array 202 may comprise a plurality of electrode contacts 208 that are arranged linearly along a length or a portion of a length of the electrode array 202, such as, for example, that shown in FIG. 2. The electrode array 202 may comprise any suitable number of contacts. As can be seen in FIG. 2, the electrode array 202 may comprise N contacts, where N can be any suitable integer from 10 to 30. In some embodiments, the electrode array 202 may comprise at least 10 electrode contacts, at least 15 electrode contacts, or at least 20 electrode contacts. In one particular embodiment, the electrode array 202 may comprise 22 electrode contacts. Each of the electrode contacts 208 may be electrically isolated from the other electrode contacts 208 and may be configured to deliver an electrical stimulation to a designated portion of the cochlea. In an operating configuration, the electrode array 202 may be inserted into the cochlea such that each contact 208 is adjacent to a portion of the cochlea, each portion corresponding to a different range of frequencies and thereby representing a different pitch that may be stimulated to a hearing-impaired patient.

The exemplary cochlear implant 200 may further comprise of a first ground electrode 210 that is suitable for placement external to the cochlea, and a second ground electrode 212 that may be positioned on, within, or near an apex of the cochlea. The first and second ground electrode 210, 212 may be any suitable type of electrodes. In one embodiment, the first ground electrode 210 may be a plate electrode. In another embodiment, the second ground electrode 212 may be a ball electrode. The first ground electrode 210 may be placed on an implant package, which may be placed external of the cochlea. The second ground electrode 212 may be surgically placed at or near the apex of the cochlea, e.g., via an apical cochleostomy.

The exemplary embodiment of a cochlear implant of the present invention may further include a processing arrangement configured to decompose an audio input signal into a plurality of frequency channels, and to map each of the electrode contacts of the electrode array to provide electrical stimulation (e.g., monopolar or other types of stimulation) to stimulate hearing of the patient in at least one frequency channel. The processing arrangement may comprise one or more computer processors configured to execute one or more sets of instructions configured to map each of the electrode contacts to one or more ground electrodes and/or control delivery of an electrical signal to stimulate hearing in the cochlea within predetermined frequency channels. The processing arrangement may also be operably connected via any suitable communications link (e.g., wired or wireless) to an external input and/or output device for interfacing with an operator. Alternatively, the cochlear implant may comprise a transmitter and a receiver, or a transceiver, configured to transmit data to an external processing arrangement and receive instructions from the external processing arrangement for mapping each of the electrode contacts to one or more ground electrodes and/or controlling delivery of an electrical signal to stimulate hearing in the cochlea within predetermined frequency channels.

The electrode array 202, along with the first and second ground electrodes 210, 212 may be operably connected to the processing arrangement configured to control delivery electrical signal delivered from by a selected electrode contact on the electrode array 202 to at least one of the first and second ground electrodes 210, 212. Each of the electrode contacts 208 on the electrode array 202 may be mapped with the first ground electrode, the second ground electrode, or with both. For example, each electrode contact 208 on the electrode array 202 may be mapped with the first and/or second electrode 210, 212 such that each combination may deliver an electrical signal that stimulates hearing in the cochlea within a different predetermined frequency channel or frequency range.

In some embodiments, for at least one or more of the electrode contacts 208 on the electrode array 202, each contact 208 may be mapped to provide electrical stimulation to stimulate hearing of the patient for two different frequency channels, corresponding to two different frequency ranges. In particular, the two different frequency channels may comprise a first frequency channel that may be stimulated at a location within a first turn from the base of the cochlea, such as for example, at a location where a normal cochlea would expect a frequency at or greater than 800 Hz, and a second frequency channel audio frequency that may be stimulated at a more apical location within the cochlea. The more apical location may be any location that is more apical than the position of the electrode contact 208 that is being mapped. For example, the more apical location may be further towards the apex of the cochlea as compared to the distal end of the electrode array 202. The more apical location may be, for example, deeper towards the apex beyond the first turn from the base of the cochlea. Typically, the first location may be adjacent to the electrode contact 208 and the second location may be more apical than the location of the electrode contact 208, thereby providing a virtual extension of the electrode's ability to provide more apical stimulation of the cochlea, with reduced risk to the patient as compared a physical extension to the length of an electrode array 202. As discussed above, extended length electrode arrays that can be physically inserted deeper towards the apex of the cochlea may increase the risk for structural damage to the cochlea during insertion thereby irreversibly harming the patient's hearing as opposed to improving it.

Figures 6A, 6B:
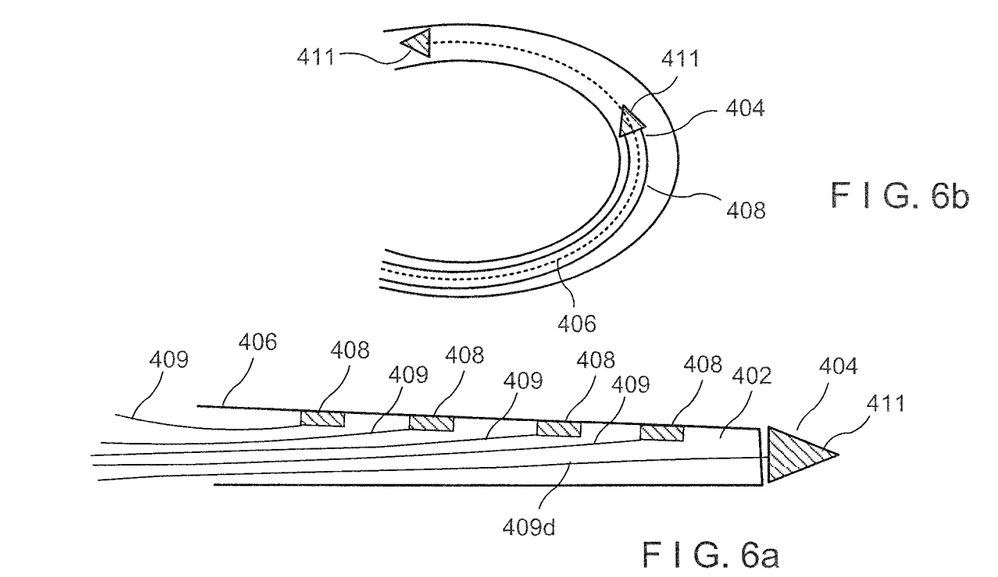
FIG. 6a shows another exemplary embodiment of an electrode array for a cochlear implant.
FIG. 6b shows an exemplary deployment of an advanceable tip of the electrode array of FIG. 6a in an apical direction.

In an alternative embodiment, an electrode array 402 having a distal end 404 and a proximal end 406 may comprise a plurality of electrode contacts 408 arranged linearly along a length or a portion of a length of the electrode array as shown in FIG. 6a. Each of the electrode contacts 408 may be electrically isolated from each other. Each electrode contact 408 may be connected to a wire 409 that is operably connected to a power source and/or a controller or processing arrangement for controlling delivery of stimulation to the cochlea via the electrode contacts. In certain embodiments, the power source and/or controller or processing arrangement may be incorporated in an implant body 401. The implant body 401, when in use, may be attached external to the cochlea of the patient and operably connected to an electrode array, an apical ground electrode and, optionally an extracochlear ground electrode, which may, for example, be attached to the implant body 401. The electrode array 402 may also include a distal most electrode contact 411 positioned at or near the distal end of the electrode array, in particular, at the distal tip of the electrode array 402. The distalmost contact 411 may comprise a component that projects distally from the distal end of the electrode array 402 (e.g., a wire stylet extendable from the distal end of the electrode array 402). The distalmost contact 411, in particular, the distally projectable component of the distalmost contact 411, may be connected to a wire 409d that is sufficiently long to allow for further apical advance of the distalmost contact 411 while operably connecting the distalmost contact to a power source and/or a controller or processing arrangement for controlling delivery of stimulation to the cochlea via the distalmost electrode 411. Therefore, this alternative embodiment of an electrode array 402 may be inserted into the cochlea and advanced more apically (and therefore into lower frequency regions of the cochlea) than the insertion depth of the electrode array, in particular, by pushing/advancing the distalmost contact 411 (e.g., wire stylet) towards the apex of the cochlea. For example, when in use, the electrode array 402 may be first inserted into a cochlea of a patient and the distalmost contact 411 may be advanced further apically after full electrode insertion, as shown in FIG. 6b. The electrode array may have any suitable length, for example, the electrode array may have a length from about 20 to about 25 mm. This alternative embodiment may be stimulated in a bipolar mode with other more proximal electrode contacts or singularly in combination with a ground electrode (e.g., an external ground electrode). In a particular exemplary embodiment, a cochlear implant may comprise a 20 to 25 mm electrode array with a tip electrode contact that can be advanced beyond the electrode insertion depth by pushing/advancing a wire stylet connected to the tip contact. This small contact could be advanced deeper (more apically) into the lower frequency regions. This contact may be stimulated in a bipolar mode with other more proximal contacts or singularly to the external ground electrode.

Figure 6C:
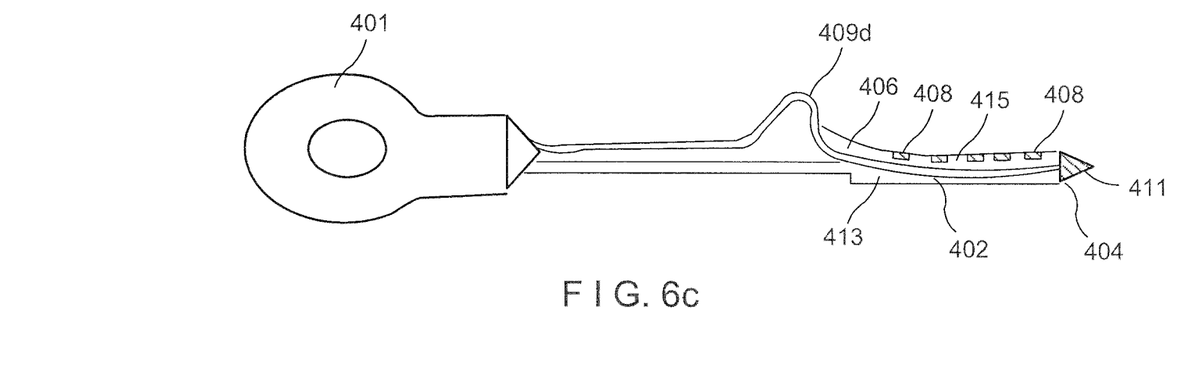
FIG. 6c shows an exemplary embodiment of a cochlear implant having the electrode array of FIG. 6a with an advanceable ground electrode.

In a particular embodiment, as shown in FIG. 6c, the electrode array 402 may further include a flexible non-conductive substrate 415 on which the plurality of electrode contacts 408 may be attached. The non-conductive substrate 415 may comprise or be formed from a shape-memory material, e.g., thermoplastic elastomers, silicone, etc. In particular, the non-conductive substrate 415 may have an elongated shape having a distal end 404 and a proximal end 406. The non-conductive substrate 415 may comprise a channel 413 extending therethrough from the distal end 404 to the proximal end 406 defining a lumen therein. The distalmost contact 411 may comprise a distally extendable component connected to an advanceable ground wire 409d. The advanceable ground wire 409d may extend from the implant body 401 through the channel 413 to the distalmost contact 411. The advanceable ground wire 409d may be sufficiently long to operably connect the distalmost contact 411 to a power source and/or a controller or processing arrangement for controlling delivery of stimulation to the cochlea via the distalmost contact 411. In particular, the advanceable ground wire 409d may be longer than wires 409 connected to the other electrode contacts 408 on the electrode 402 array so as to accommodate additional advancement of the distalmost contact 411 towards the apex of the patient's cochlea.

Another aspect of the present application is a new fitting (mapping) technique for cochlear implant users. A typical mapping for a cochlear implant involves mapping a frequency range to each of the electrode contacts in an array. In the new fitting strategy, a frequency range may now be mapped to a combination of an intra-cochlear electrode contact and a ground electrode, whether it be an extracochlear ground electrode or an apical ground electrode. In other words, the lowest frequencies (such as, for example, 75-150 Hz) could be mapped to the most apical electrode on the electrode array with use of the apical ground electrode as the accompanying ground electrode. The next lowest frequencies (such as, for example, 150-300 Hz) could also be mapped to the most apical electrode on the electrode array and with use of an extra-cochlear ground electrode as the accompany ground electrode. Alternatively, 150-300 Hz could be mapped to the second most apical electrode using the apical ground electrode for a ground. Perceptual experiments may be conducted to determine the optimal mapping configuration.

In one exemplary embodiment, a method for fitting an exemplary cochlear implant as discussed above may be provided. The fitting process may include repeated hearing tests administered to the patient post-surgery to map and adjust the mapping of each electrode contact to at least one audio frequency range. For example, a first audio signal at a first frequency may be administered and mapped to an electrode contact. Subsequently, a second audio signal at a different frequency may be administered and mapped to the same or a different electrode contact. This may be repeated for as many different frequencies as needed. The fitting process for each electrode contact may also include selection of either the first ground electrode or the second ground electrode to be used to impart an electrical stimulus to the cochlea. The first ground electrode, which is positioned external to the cochlea, may be selected when the frequency of the audio signal is high. In contrast, the second ground electrode, which is positioned in or near the apex of the cochlea, may be selected when the frequency of the audio signal is low. The low frequency audio signal may tonotopically correspond to a more apical location within the cochlea as discussed above. Furthermore, the electrode array may be mapped according to a frequency allocation table, where each electrode contact on an array is assigned to at least one different frequency channel or frequency range, in the manner described above. In some embodiments, at least one electrode contact is assigned to two different frequency channels or frequency ranges. The mapping of the frequency allocation table may be performed within a predetermined period of time.

In one exemplary embodiment, the electrode array may comprise a predetermined number of electrode contacts, and a plurality of frequency channels may be mapped to the electrode contacts of the electrode array, in particular, the number of frequency channels may be greater than the predetermined number of electrode contacts. For example, the electrode array may comprise 22 electrode contacts, which may be mapped to more than 22 frequency channels, such as for example, 44 frequency channels.

The present application also provides a new method which may be used to provide apical stimulation without increasing the length of the electrode array inserted into the cochlea. Typically, cochlear implants provide stimulation on one intra-cochlear electrode contact and ground the stimulation to an electrode external to the cochlea. A cochlear implant may include two electrodes that are designed to be used as extra cochlear grounds to allow for redundancy or to provide separate extra cochlear electrodes for stimulation and recording when measuring neural responses within the cochlea. One of the electrodes designed to be an extracochlear ground may be implanted inside the apex of the cochlea via an apical cochleostomy (ApexEl) as illustrated in an exemplary embodiment shown in FIGS. 2 and 3. If so, stimulation may be provided from any electrode contact 208 (e.g., Array1, Array2, . . . ArrayN) on the electrode array 202 to either the ground electrode located near the apex 212 (ApexEl) or the remaining extra cochlear electrode 210 (ExtraCochlear) as illustrated in the exemplary embodiments shown in FIGS. 2 and 3.

More specifically, FIG. 3 shows placement of the Apical Electrode contact 212(ApexEl) relative to the electrode array 202 and extra cochlear electrode 210. FIG. 3 shows electrode contacts and labelled as further described below. Electrode contacts 208 placed on an exemplary cochlear implant electrode array 202 as shown in FIGS. 2 and 3 are labeled Array1, Array2 ArrayN where Array1 204 is the most apical of the electrode contacts on the intracochlear array 202 and ArrayN 206 is the most basal of the electrode contacts 208 on the intracochlear electrode array 202. The electrode contact 212 placed in the apex via a cochleostomy is labeled ApexEl. The extra cochlear electrode 210 is positioned away from the array 202 and is labeled Extra-Cochlear.

Stimulation using ExtraCochlear 210 as a ground electrode may provide stimulation to portions of the cochlea to which an electrode contact may be adjacent. However, stimulation from any one of the electrode contacts 208 on the electrode array 202 (ArrayX) to ApexEl 212 may route the electrical stimulation, e.g., current, towards the apex of the cochlea. It is believed that this will provide more apical stimulation.

Using this new approach, a cochlear implant 200 sound processing strategy may use stimulation from ArrayN 206 to either ApexEl 212 or ExtraCochlear 210 as separate channels. Alternatively, ArrayN 206 may provide stimulation to either ApexEl 212 or ExtraCochlear 210 simultaneously. Both of these options would allow a potential increase in the number of channels provided to the cochlear implant user. Additionally, electrode contacts 208 on the apical end of the array 202 (e.g., Array1 or Array2) that are grounded to ApexEl 212 may provide stimulation at cochlear locations beyond the most apical electrode 204 on the array (Array1), effectively extending the functional length of the electrode array 202 without increasing the physical length of the array 202.

One implementation of a speech coding strategy may be to use a standard envelope extracting algorithm. Any suitable envelope extracting methods may be used, for example, advanced combination encoder (ACE) or continuous interleaved sampling (CIS) methodologies, such as those commercially available from Cochlear Corporation. In this case, the lowest frequency channels may be associated with electrode contacts 208 relatively apically located on the array 202 and grounded by the apical electrode 212. The same electrode contacts 208 on the cochlear implant array 202 may be mapped to either apical 212 or extra-cochlear 210 ground electrodes.

An exemplary signal processing method (e.g., utilizing CIS or other suitable envelop extracting methods) with a cochlear implant may include any suitable number of channels and/or electrode contacts. In one exemplary embodiment, the method may utilize 4 channels and 4 corresponding electrode contacts arranged linearly along an electrode array. Although the CIS signal processing method is described herein with respect to 4 channels and 4 corresponding electrode contacts, it is contemplated that any suitable number of channels and/or electrode contacts (e.g., 12, 15, or 22) for a cochlear implant may be used. An initial audio input signal may be received and processed using a bandpass filter, in which the input signal is separated by different ranges of audio frequencies to the 4 different channels. The bandpass filters are such that usually there is one filter for each electrode contact. For each channel, the envelope of the bandpass filtered signal, which is within the desired range for each channel, may be extracted and converted to a series of pulses representing the amplitude of the bandpass filtered signal at any given moment of time. The pulses may be presented to each of the corresponding electrode contacts implanted into a cochlea of a patient, where each contact is located at a different position along the spiral shape of the cochlea. Specifically, the filter representing the lowest frequencies yields an output on the most apically implanted electrode contact of the array. The filter representing the second lowest set of frequencies will result in instructions for stimulating the second most apical electrode, etc. In one particular example, the frequencies for a cochlear implant may include 12 channels, each corresponding to a different range of frequencies to which the input signal may be bandpass filtered to correspond to 12 differently placed electrode contacts inserted into the cochlea.

The new apical channels (produced by stimulating between the apical ground and the electrode array) could be used for encoding lower frequencies using a temporal or fine structure algorithm instead of an envelope extraction.

In another example, the circuitry in the cochlear implant may be modified to produce stimulation directly from the apical electrode 212 (ApexEl). This may allow stimulation from ApexEl 212 to ExtraCochlear 210, providing an additional site of stimulation that could be even more apical than stimulation between the apical electrode 212 and an intracochlear electrode or electrode contact 208.

In a further example, stimulation may be provided independently on each electrode contact 208. For example, each electrode contact 208 may be connected to an independent current source. In this situation, the apical electrode 212 (ApexEl) may be used to shape the electrical field. For example, stimulation from Array1 204 may be routed completely to ApexEl 212, or a combination of ApexEl 212 and ExtraCochlear 210. The relative weighting of current going to ApexEl 212 and ExtraCochlear 210 may determine the shape of the spread of excitation with some intermediary shape between the field created by Array1→ApexEl stimulation and Array1→ExtraCochlear stimulation. Additionally, current steering could be provided between ApexEl 212 and other combinations of ExtraCochlear 210 and any of the electrode contacts 208 on the array 202 (ArrayX).

Additional apical channels provided by the new configuration may also be used to provide lower frequencies than are typically encoded by a conventional system. This would leave the mismatch between spiral ganglion place and the corresponding frequency delivered by the implant at that location as is but would provide a greater range of frequencies to the listener.

As described above, in some exemplary embodiments of a cochlear implant, at least two ground electrodes may be included, one of which may be placed at or near the apex of the cochlea. If the most apical electrode contact 204 in an array 202 (Array1) is stimulated with the apical ground electrode 212 (ApexEl), the current would flow from Array1 202 up the cochlea. Therefore, an electrode contact 208 within an electrode array 202 as described herein could be used with either an extracochlear ground electrode 210 or an apical ground electrode 210, in the alternative, to provide stimulation at two different possible cochlear locations. Therefore, a single electrode contact within the electrode array 202 may be used to provide electrical stimulation to two different possible locations in the cochlea, depending on which ground electrode is used in combination with the electrode contact 208. Therefore, additional bandpass filters may also be used to separate input signals to additional frequency channels that may be stimulated at these additional locations. For example, if the electrode array includes 22 electrode contacts and all 22 electrode contacts may be used in both modes (e.g., with an apical ground electrode or with an extracochlear ground electrode), a total of 44 frequency channels and therefore 44 bandpass filters may be used. In some embodiments, frequency channels having the lowest frequencies may be stimulated using electrode contacts that are more apically positioned on the electrode array 202 in combination with a ground electrode in the apex 212, while frequency channels having the highest frequencies would be stimulated using electrode contacts 208 that are more basally positioned on the electrode array in combination with an extracochlear ground electrode 210. Examples of this new relationship are provided in FIG. 4, as further discussed below. It is contemplated that not all electrode contacts need to operate in both modes. Rather, a portion of the contacts may be able to operate in both modes, while other contacts may be configured to operate with only one of the two ground electrodes.

Figure 4:
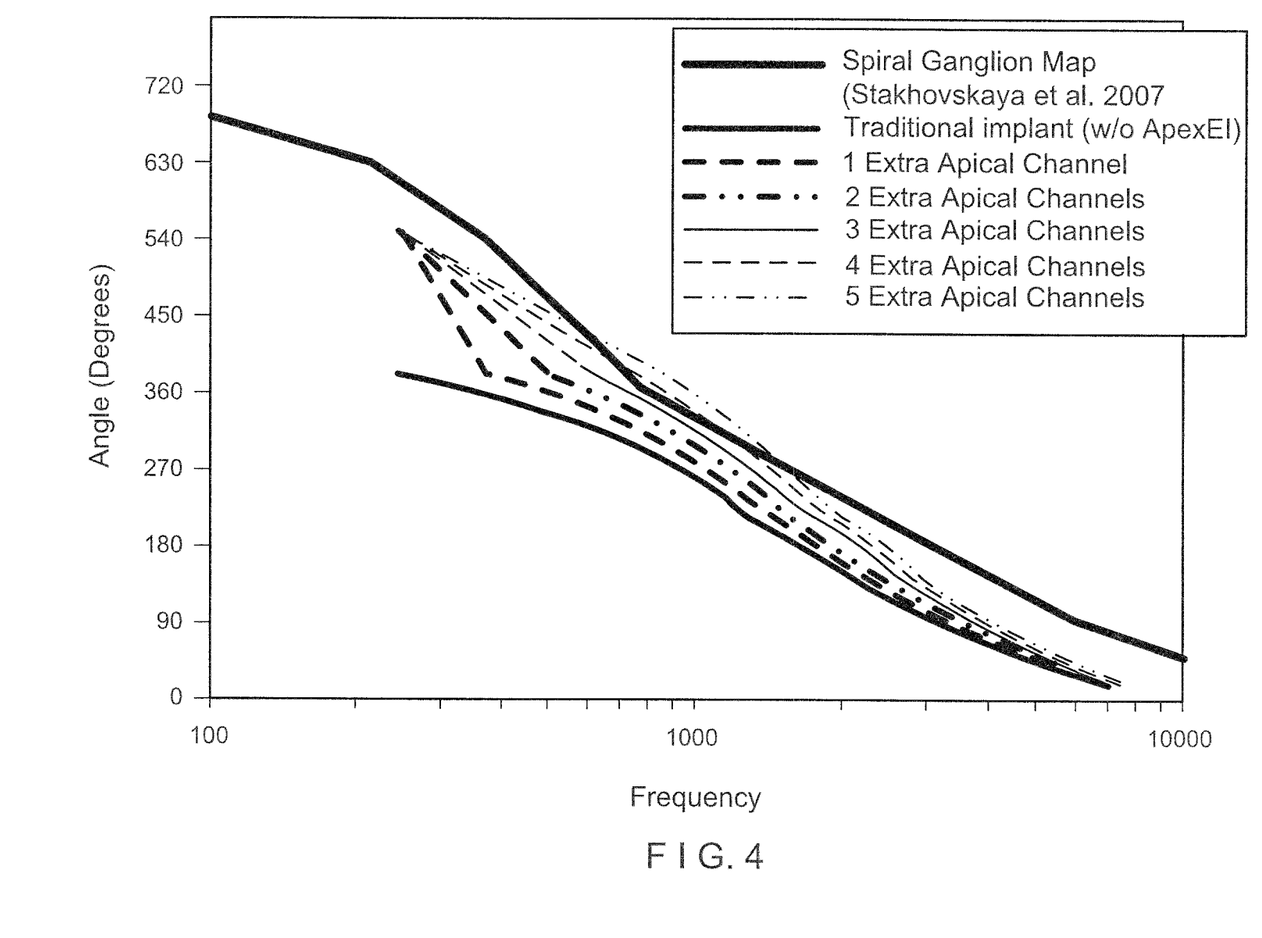
FIG. 4 shows an exemplary relationship between the frequency expected at a given cochlear angle by the spiral ganglion and the frequency provided at the same angle by the cochlear implant.

FIG. 4 shows a relationship between the frequency expected at a given cochlear angle by the spiral ganglion (top line) and the frequency provided at the same angle by the cochlear implant. For a cochlear implant without ApexEl, the y-axis indicates an example of where each electrode on the array might be placed (in degrees) and the x-axis indicates the center frequency provided at the corresponding electrode. If one additional apical channel is created by stimulating from Array1 to ApexEl and the most apical channel is now routed to the Apex1→ApexEl, FIG. 4 shows that the cochlear extent represented by the intracochlear electrodes (Array1 . . . ArrayN) shifts towards the spiral ganglion (green) line because the frequency range represented by Array1 . . . ArrayN is missing the lowest frequencies (which have been rerouted to the new Array1→ApexEl channel. FIG. 4 also shows additional examples where additional apical channels (such as including Array2→ApexEl) may be included such that the range represented by the intracochlear electrodes (Array1 . . . ArrayN) and the range represented by stimulation incorporating ApexEl moves further towards the top line as additional apical stimulation channels are added.

The same frequency range typically used by a cochlear implant may be used with the new configuration. However, with the addition of new apical channels, the fixed frequency range may be spread over a greater portion of the cochlea (FIG. 4). Some of the advantages may include: Apical stimulation might result in better sound quality and performance; Deviations from spiral ganglion may be smaller— this may make it easier for the auditory system to process resulting in a) shorter times for the subject to reach asymptotic performance and b) better asymptotic results; and as the cochlear region represented by a fixed frequency range may be increased, the spacing between two fixed frequencies along the cochlea may increase in angle along the cochlea. The result is believed to be that it will be easier for the listener to discriminate the two frequencies and will provide better spectral resolution. In another example, a method for electrically stimulating a cochlea of a hearing-impaired patient may be provided. The method may be performed by any suitable processing arrangement for directing stimulation of a cochlea by a cochlear implant. For example, a receiving arrangement or the cochlear implant may receive an input audio signal that is to be processed to generate corresponding electrical stimulations to the cochlea of the patient. The input audio signal may be any form of audio that is to be heard by the patient, such as, for example, speech. The input audio signal may be decomposed into a plurality of frequency channels, each frequency channel corresponding to a different range of audio frequencies. Each frequency channel may be mapped to an electrode contact and a ground electrode. Therefore, for stimulation in a desired frequency channel a stimulation (e.g., monopolar or other types of stimulation) may be provided from an electrode contact on the electrode array to a ground electrode to stimulate hearing of the patient within the frequency range of the desired frequency channel. The method may select one of the two available ground electrodes depending on the frequency range of the frequency channel. The first ground electrode, which is positioned external to the cochlea, may be selected when the frequency range is high. In contrast, the second ground electrode, which is positioned in or near the apex of the cochlea, may be selected when the frequency range is low. The low frequency audio signal may tonotopically correspond to a more apical location within the cochlea as discussed above.

Those skilled in the art will understand that the exemplary embodiments described herein may be implemented in any number of manners, including as a separate software module, as a combination of hardware and software, etc. For example, the exemplary analysis methods may be embodiment in one or more programs stored in a non-transitory storage medium and containing lines of code that, when compiled, may be executed by at least one of the plurality of processor cores or a separate processor. In some embodiments, a system comprising a plurality of processor cores and a set of instructions executing on the plurality of processor cores may be provided. The set of instructions may be operable to perform the exemplary methods discussed below. The at least one of the plurality of processor cores or a separate processor may be incorporated in or may communicate with any suitable electronic device, for example, a cochlear implant, a mobile computing device, a smart phone, a computing tablet, a computing device, etc.

Figure 5:
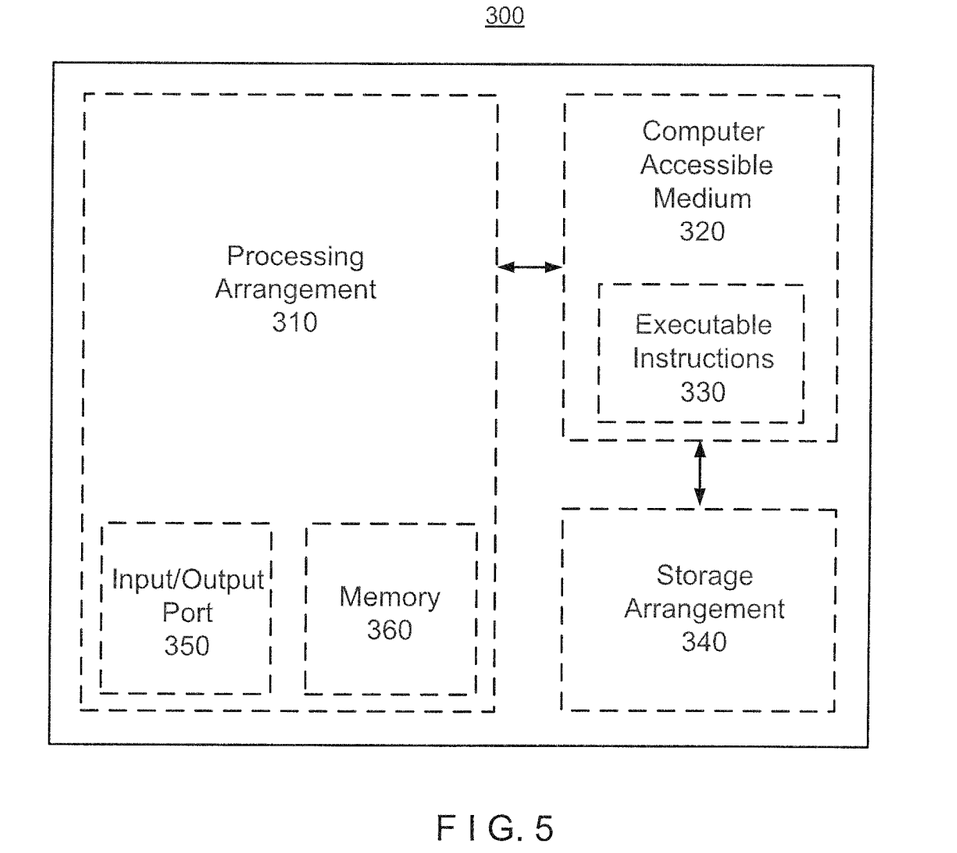
FIG. 5 illustrates an exemplary computer system for performing a method for electrically stimulating a cochlea of a hearing-impaired patient or a method for fitting a cochlear implant.

For example, the exemplary methods may be embodied in an exemplary system 300 as shown in FIG. 5. The exemplary system 300 may be part of an implant body attached external to a cochlea of a patient and operably connected to an electrode array, an apical ground electrode and, optionally an extracochlear ground electrode, which may, for example, be attached to the implant body. Alternatively, all or parts of the system 300 may be incorporated within a cochlear implant that is inserted into the cochlea of a patient with in an operative configuration. An exemplary method described herein may be performed entirely or in part by a processing arrangement 310. For example, the system 300 may be configured to decompose an audio input signal into a plurality of frequency channels, and to map each of the electrode contacts of the electrode array to provide electrical stimulation (e.g., monopolar or other types of stimulation) to stimulate hearing of the patient in at least one frequency channel. The system 300 may also be operably connected via any suitable communications link (e.g., wired or wireless) to an external input and/or output device for interfacing with an operator. Alternatively, the system 300 may be configured to receive audio input data from a cochlear implant or a microphone, and to transmit instructions to a cochlear implant for mapping each of the electrode contacts to one or more ground electrodes and/or controlling delivery of an electrical signal to stimulate hearing in the cochlea within predetermined frequency channels.

Such processing/computing arrangement 310 may be, e.g., entirely or a part of, or include, but not limited to, a computer/processor that can include, e.g., one or more microprocessors, and use instructions stored on a computer-accessible medium (e.g., RAM, ROM, hard drive, or other storage device). As shown in FIG. 5, e.g., a computer-accessible medium 320 (e.g., as described herein, a storage device such as a hard disk, floppy disk, memory stick, CD-ROM, RAM, ROM, etc., or a collection thereof) can be provided (e.g., in communication with the processing arrangement 310). The computer-accessible medium 320 may be a non-transitory computer-accessible medium. The computer-accessible medium 320 can contain executable instructions 330 thereon. In addition or alternatively, a storage arrangement 340 can be provided separately from the computer-accessible medium 320, which can provide the instructions to the processing arrangement 310 so as to configure the processing arrangement to execute certain exemplary procedures, processes and methods, as described herein, for example.

The system 300 may also include a receiving arrangement (now shown) for receiving an input audio signal, e.g., an audio receiver or a microphone. The receiving arrangement may be part of a larger device, e.g., a cochlear implant. The system 300 may further transmit instructions for administering electrical stimulus to a cochlear implant, in particular, a cochlear implant having a plurality of electrode contacts on an electrode array along with an apical ground electrode and/or an extracochlear ground electrode. The cochlear implant may include a microphone, a signal processor, one or more electrode contacts, and/or one or more computer processors for performing a portion or the entirety of the methods described above.

The invention described and claimed herein is not to be limited in scope by the specific embodiments herein disclosed since these embodiments are intended as illustrations of several aspects of this invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims. All publications cited herein are incorporated by reference in their entirety.

What is claimed is:

1. A cochlear implant, comprising:
a first ground electrode configured to be positioned external to a cochlea of a patient;
a second ground electrode configured to be positioned in or adjacent to an apex of a cochlea of a patient;
a flexible electrode array having a distal end and a proximal end defining a length therebetween, the electrode array comprising a plurality of electrode contacts arranged along at least a portion of the length of the electrode array, wherein the electrode array is configured to be inserted into the cochlea such that the distal end of the electrode array advances from a base of the cochlea towards the apex of the cochlea; and
a processing arrangement configured to map at least one of the electrode contacts to a first mapping for providing a first electrical stimulation from the electrode contact to the first ground electrode to stimulate hearing of the patient at a first location in the cochlea, and a second mapping for providing a second electrical stimulation from the electrode contact to the second ground electrode to stimulate hearing of the patient at a second location in the cochlea,
wherein the first location in the cochlea is positioned adjacent to the electrode contact when the implant is inserted into the cochlea in an operating position, and the second location in the cochlea is positioned further towards the apex of the cochlea as compared to the distal end of the electrode array when the implant is in the operating position.

2. The cochlear implant of claim 1, wherein the length of the electrode array is configured to be inserted by no more than about 450 degrees into the cochlea towards the apex.

3. The cochlear implant of claim 2, wherein the length of the electrode array is configured to be inserted by no more than about 360 degrees into the cochlea towards the apex.

4. The cochlear implant of claim 1, wherein the first electrical stimulation is a monopolar electrical stimulation.

5. The cochlear implant of claim 1, wherein the second electrical stimulation is a monopolar electrical stimulation.

6. The cochlear implant of claim 1, wherein the first ground electrode is a plate electrode.

7. The cochlear implant of claim 1, wherein the second ground electrode is a ball electrode.

8. The cochlear implant of claim 1, wherein the electrode array is biased to a snail-like coiled shape.

9. The cochlear implant of claim 1, wherein the second electrical stimulation imparts hearing to a patient at a lower frequency than hearing imparted by the first electrical stimulation.

10. The cochlear implant of claim 1, wherein the length of the electrode array is less than approximately 31 mm.

11. A method for fitting a cochlear implant, comprising:
administering a first audio signal having a first frequency to a patient implanted with the cochlear implant, the implant comprising a first ground electrode positioned external to a cochlea of a patient, a second ground electrode positioned in or adjacent to an apex of the cochlea of the patient, and an electrode array having a distal end and a proximal end defining a length therebetween, the electrode inserted into the cochlea such that the distal end of the electrode array is advanced from a base of the cochlea towards the apex of the cochlea;
mapping a first one of the electrode contacts with the first ground electrode for imparting a first electrical signal configured to stimulate hearing of the patient at a first frequency channel;
administering a second audio signal having a second frequency to the patient implanted with the cochlear implant; and
mapping the first electrode contact with the second ground electrode for imparting a second electrical signal configured to stimulate hearing of the patient at a second frequency channel having a lower frequency range as compared to the first frequency channel.

12. The method of claim 11, wherein the second frequency channel is stimulated by the first electrode contact to a location in the cochlea positioned further towards the apex of the cochlea as compared to the distal end of the electrode array.

13. A non-transitory computer-readable storage medium including a set of instructions executable by a processor, the set of instructions, when executed by the processor, causing the processor to perform steps of claim 11.

* * * * *

UNITED STATES PATENT AND TRADEMARK OFFICE
CERTIFICATE OF CORRECTION

PATENT NO. : 10,874,848 B2
APPLICATION NO. : 16/015041
DATED : December 29, 2020
INVENTOR(S) : Landsberger et al.

It is certified that error appears in the above-identified patent and that said Letters Patent is hereby corrected as shown below:

In the Claims

Claim 11, Column 17, Lines 10-11:
"distal end and a proximal end defining a length therebetween, the electrode inserted into the cochlea such" should read "distal end and a proximal end defining a length therebetween, the electrode array inserted into the cochlea such".

Signed and Sealed this
Ninth Day of March, 2021

Drew Hirshfeld
*Performing the Functions and Duties of the*
*Under Secretary of Commerce for Intellectual Property and*
*Director of the United States Patent and Trademark Office*